(12) United States Patent
Studer et al.

(10) Patent No.: US 6,812,368 B2
(45) Date of Patent: Nov. 2, 2004

(54) DIASTEREOSELECTIVE HYDROGENATION OF 1,3-HYDROXYKETONES

(75) Inventors: Martin Studer, Basel (CH); Stephan Burkhardt, Gelterkinden (CH); Ulrike Nettekoven, Basel (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/610,919

(22) Filed: Jul. 2, 2003

(65) Prior Publication Data

US 2004/0010154 A1 Jan. 15, 2004

(30) Foreign Application Priority Data

Jul. 2, 2002 (EP) ............................................. 02014097
May 27, 2003 (EP) ............................................. 03101541

(51) Int. Cl.[7] ............................................. C07C 27/04
(52) U.S. Cl. ........................ 568/862; 549/313; 560/60; 560/186; 564/201
(58) Field of Search ........................ 568/862; 564/201; 549/313; 560/186, 60

(56) References Cited

U.S. PATENT DOCUMENTS 5,347,039 A 9/1994 Leon et al.

OTHER PUBLICATIONS

Faizulla G. Kathawala, et al., "Stereoselective Reduction of δ–Hydroxy–β–ketoesters", Helvetica Chimica Acta., vol. 69, No. 4, pp. 803–805, Jun. 18, 1986, XP002145104 Verlag Helvetica Chimica Acta., Basel, CH. ISSN: 0018–019X.

Véronique Blandin et al., "Asymmetric Hydrogenation of 2,4–Dioxo Esters: Selective Synthesis of 2–Hydroxy–4–oxo Esters and Direct Access to Chiral 2–Hydroxy–4–butyrolactones", European Journal of Organic Chemistry, pp. 1787–1793, 1999, XP002221217, Wiley–VCH Verlag, Weinheim, DE ISSN: 1434–193X.

Koichi Narasaka et al., "Stereo Reduction of β–Hydroxyketones to 1,3–Diols", Tetrahedron, vol. 40, No. 12, pp. 2233–2238, 1984, XP002221218, Elsevier Science Publishers Amsterdam, NL ISSN: 0040–4020.

*Primary Examiner*—Michael L. Shippen
(74) *Attorney, Agent, or Firm*—Wenderoth, Lind & Ponack, L.L.P.

(57) ABSTRACT

The invention relates to a novel process of diastereoselective hydrogenation of 1,3-hydroxyketones of formula (I)

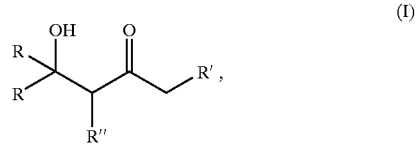

(I)

wherein R, R' and R" are as defined in claim 1 which is carried out in a solvent in the presence of a magnesium salt, a heterogeneous platinum catalyst and optionally an oxidant.

10 Claims, No Drawings

DIASTEREOSELECTIVE HYDROGENATION OF 1,3-HYDROXYKETONES

This invention relates to a novel process of diastereoselective hydrogenation of 1,3-hydroxyketones.

Stereoselective preparation of the 1,3-diol function has great utility in organic chemistry due to the occurrence of such a group in natural products. Besides enzymatic routes, there are also transition-metal-catalysed hydrogenation reactions described. For example, in *Eur. J. Org. Chem.* 1999, 1787–1793, the enantioselective homogeneous catalysis using rhodium- or ruthenium-bisphosphane complexes are described. However, the different proposed routes are not fully satisfactory.

It is therefore an object of the instant invention to provide for a hydrogenation process using a simple, commercially available heterogeneous catalyst which can be filtered off after the reaction. It is a further object that the process has a good selectivity and that the hydrogenation proceeds fast. It is also an object to provide for a process not using expensive compounds. A further object is a process which does not necessarily require low temperature thus avoiding cooling equipment. An even further object is a process whereby the waste problems are minimised.

Surprisingly, it has now been found that the addition of magnesium salts to a heterogeneous catalytic system based on platinum catalysts significantly improves the diastereoselective hydrogenation of 1,3-hydroxyketones. A further surprising improvement, especially with regard to the overall conversion and the diastereomeric ratio is observed when a catalytic amount of an oxidant such as $H_2O_2$ is added to the reaction mixture.

In general, the beneficial effects of the inventive reaction are observed for a large structural variety of 1,3-hydroxyketones and in general at least an increase in the conversion is observed by the addition of a magnesium salt and the optional addition of a catalytic amount of an oxidant. Such increase is in particular also observed for acyl derivatives of 1,3-hydroxyketones and 1,3-hydroxyketones which are twice substituted in the 2-position.

The invention especially relates to a process, wherein a compound of formula (I)

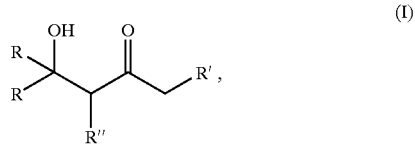

wherein R, R' and R" are independently of each other a radical being compatible with the reaction conditions, except compounds wherein a) one R is H and the other R is —$CH_2CN$, R" is H and R' is —C(=O)$OR_b$ and $R_b$ is a H or a carboxy-protecting group;

b) one R is H and the other R is —$CH_2C$(=O)NR*R**, R" is H and R' is —C(=O)$OR_b$ and R* and R** are independently of each other H or an amide-protecting group and $R_b$ is H or a carboxy-protecting group;

c) one R is H and the other R is —$CH_2C$(=O)$OR_b$, R" is H and R' is —$CH_2$—$N_3$ and $R_b$ is H or a carboxy-protecting group; and d) one R is H and the other R is —$CH_2C$(=O)$OR_b$, R" is H and R' is —$CH_2$—$R_d$ and $R_b$ is H or a carboxy-protecting group and $R_d$ is halogen;

is reduced with hydrogen to the corresponding diol, which is predominantly in the form of the syn-diol, in the presence of a magnesium salt and a heterogeneous platinum catalyst in a solvent.

Unless otherwise indicated, halogen is preferably fluorine, chlorine, bromine or iodine.

Suitable compatible radicals R, whereby the two radicals R must be different from each other, are for example H, alkyl, haloalkyl, hydroxyalkyl, alkoxyalkyl, haloalkoxy, cycloalkyl, cycloalkoxy, cycloalkyl-alkyl, cycloalkylalkoxy, aryl, aryloxy, aralkyl, aralkoxy, —$CH_2CO_2R_4$, —$CHR_4CO_2R_5$, —$CO_2R_4$, —$CH_2C(O)NH_2$, —$CH_2C(O)NHR_4$, —$CH_2C(O)NR_4R_5$, —$CHR_4C(O)NH_2$, —$CHR_4C(O)NHR_5$, —$CHR_4C(O)NR_5R_6$, —C(O)—$NH_2$, —C(O)—$NHR_4$ and —C(O)—$NR_4R_5$, wherein $R_4$, $R_5$ and $R_6$ are independently from each other alkyl, cycloalkyl, cycloalkylalkyl, phenyl or benzyl; to the extent possible said radicals may be branched or unbranched and may be unsubstituted or substituted. Preferred radicals R are H, alkyl (most preferred $C_1$–$C_{12}$-alkyl), aryl (most preferred phenyl or naphthyl), —$CH_2CO_2R_4$, —$CHR_4CO_2R_5$, —$CO_2R_4$, —$CH_2C(O)NH_2$, —$CH_2C(O)NHR_4$, —$CH_2C(O)NR_4R_5$, —$CHR_4C(O)NH_2$, —$CHR_4C(O)NHR_5$, —$CHR_4C(O)NR_5R_6$, —C(O)—$NH_2$, —C(O)—NHR and —C(O)—$NR_4R_5$ which independently of each other may be unsubstituted or substituted. Also preferred are compounds where at least one radical R is H or lower alkyl, whereby H is particularly preferred. Suitable substituents are apparent from the given lists of compatible radicals and protecting groups. Preferred substituents are halogen, oxygen, nitrogen, hydroxy and lower alkoxy.

Suitable compatible radicals R' or R" are for example H, alkyl, alkoxy, haloalkyl, hydroxyalkyl, alkoxyalkyl, haloalkoxy, cycloalkyl, cycloalkoxy, cycloalkyl-alkyl, cycloalkylalkoxy, aryl, aryloxy, aralkyl, aralkoxy, halogen, —OH, —$OR_4$, —OC(O)$R_4$, —NH—C(O)—$R_4$, —$NR_4$—C(O)—$R_4$, —$CO_2R_4$, —C(O)—$NH_2$, —C(O)—$NHR_4$, and —C(O)—$NR_4R_5$, wherein $R_4$ and $R_5$ are independently from each other alkyl, cycloalkyl, cycloalkylalkyl, phenyl or benzyl; to the extent possible said radicals may be branched or unbranched and may be unsubstituted or substituted. Preferred radicals R' are H, alkyl (most preferred $C_1$–$C_{12}$-alkyl), aryl (most preferred phenyl or naphthyl), —$CO_2R_4$, —C(O)—$NH_2$, —C(O)—$NHR_4$, and —C(O)—$NR_4R_5$ which may be unsubstituted or substituted. Preferred radicals R" are H, alkyl (most preferred $C_1$–$C_{12}$-alkyl), cycloalkyl and aryl (most preferred phenyl or naphthyl) which independently of each other may be unsubstituted or substituted. Suitable substituents are apparent from the given lists of compatible radicals and protecting groups. Preferred substituents are halogen, oxygen, nitrogen, hydroxy and lower alkoxy.

The prefix "lower-" or "lower" indicates that the radical in question contains preferably up to 7 carbon atoms, especially up to 4 carbon atoms. Lower alkyl is therefore preferably $C_1$–$C_7$-alkyl, especially $C_1$–$C_4$-alkyl, and may be unbranched or branched one or more times, insofar as possible. Cyclic radicals, such as cycloalkyl, have at least 3 carbon atoms, especially from 3 to 7.

Carboxy-protecting groups are especially ester-forming, enzymatically and/or chemically removable protecting groups, preferably enzymatically and/or chemically removable protecting groups, such as heptyl, 2-N-(morpholino)ethyl, cholinyl, methoxyethoxyethyl or methoxyethyl; or those which are primarily chemically removable, e.g. alkyl, such as lower alkyl, especially methyl, ethyl, substituted lower alkyl (except for benzyl and substituted benzyl), such as substituted methyl, especially 9-fluorenylmethyl, methoxymethyl, methoxyethoxymethyl, methylthiomethyl, 2-(trimethylsilyl)ethoxymethyl, benzyloxymethyl, pivaloyloxymethyl, phenylacetoxymethyl, triisopropylsilylmethyl, 1-3-dithianyl-2-methyl, dicyclopropylmethyl, acetonyl, phenacyl, p-bromophenacyl, α-methylphenacyl, p-methoxyphenacyl, desyl, carbamidomethyl, p-azobenzenecarboxamidomethyl, N-phthalimidomethyl or 4-picolyl, 2-substituted ethyl, especially 2-iodo-, 2-bromo- or 2-chloro-ethyl, 2,2,2-trichloroethyl, 2-(trimethylsilyl)ethyl, 2-methylthioethyl, 2-(p-nitrophenylsulfenyl)ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl or 2-cyanoethyl, tert-butyl, 3-methyl-3-pentyl, 2,4-dimentyl-3-pentyl or ω-chloro-lower alkyl, especially 4-chlorobutyl or 5-choropentyl, cyclopentyl, cyclohexyl, lower alkenyl, especially allyl, methallyl, 2-methylbut-3-en-2-yl, 3-methylbut-2-enyl or 3-buten-1-yl, substituted lower alkenyl, especially 4-(trimethylsilyl)-2-buten-1-yl, cinnamyl or α-methylcinnamyl, lower alkynyl, such as prop-2-ynyl, phenyl, substituted phenyl, especially 2,6-dialkylphenyl, such as 2,6-dimethylphenyl, 2,6-diisoproylphenyl, 2,6-di-tert-butyl-4-methylphenyl, 2,6-di-tert-butyl-4-methoxyphenyl, p-(methylthio)phenyl or pentafluorophenyl, benzyl, substituted benzyl, especially triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2-6-dimethoxybenzyl, 4-(methylsulfinyl)benzyl, 4-sulfobenzyl, 4-azidomethoxybenzyl, 4-{N-[4,4-dimethyl,2,6-dioxocyclohexylidene)-3-methylbutyl]amino}benzyl, piperonyl or p-polymer-benzyl, tetrahydropyranol, tetrahydrofuranyl, or silyl radicals, such as tri-lower alkylsilyl, especially trimethylsilyl, triethylsilyl, tert-butyldiemethylsilyl, isopropyldimethylsilyl or di-tert-butylmethylsilyl, or phenyl-di-lower alkylsilyl, such as phenyldimethylsilyl; alternatively a carboxy group can also be protected in the form of an oxazolyl, 2-alkyl-1,3-oxazolinyl, 4-alkyl-5-oxo-1,3-oxazolodinyl or 2,2-bistrifluoromethyl-4-alkyl-5-oxo-1,3-oxazolodinyl radical.

Amide-protecting groups are especially allyl, tert-butyl, N-methoxy, N-benzoyloxy, N-methylthio, triphenylmethylthio, tert-butyldimethylsilyl, triisopropylsilyl, 4-(methoxymethoxy)phenyl, 2-methoxy-1-naphthyl, 9-fluorenyl, tert-butoxycarbonyl, N-benzyloxycarbonyl, N-methoxy- or N-ethoxy-carbonyl, toluenesulfonyl, N-buten-1-yl, 2-methoxycarbonylvinyl, or especially alkyl, such as lower alkyl, or more especially substituted alkyl, especially benzyl, benzyl substituted by one ore more radicals selected from lower alkoxy, such as methoxy, lower alkanoyloxy, such as acetoxy, lower alkylsulfinyl, such as methylsulfinyl, dicyclopropylmethyl, methoxymethyl, methylthiomethyl and N-benzoyloxymethyl; or bis (trimethylsilyl)methyl, trichloroethoxymethyl, tert-butyldimethylsilyloxymethyl, pivaloyloxymethyl, cyanomethyl, benzyl, 4-methoxybenzyl, 2,4-dimethoxybenzyl, 3,4-dimethoxybenzyl, 2-acetoxy-4-methoxybenzyl, o-nitrobenzyl, bis(4-methoxyphenyl) phenylmethyl, bis(4-methylsulfinylphenyl)methyl, pyrrolidinomethyl, diethoxymethyl, 1-methoxy-2,2-dimethylpropyl or 2-(4-methylsulfonyl)ethyl.

It is a characteristic of protecting groups that they are simple to remove (that is to say without undesirable secondary reactions taking place), for example by solvolysis, reduction, photolysis or alternatively under conditions analogous to physiological conditions, for example enzymatically.

The instant hydrogenation process yields predominantly syn-diols. Depending on the substrate (compound of formula (I)) and the process conditions the syn-diol exceeds, for example, 60%, preferably 70% and most preferred 90%, of the total diol produced.

Suitable solvents are alcohols, especially lower alkanoles such as methanol, ethanol, propanol or butanol, or ethylenglykol, diethylenglykol, ethylenglykolmonomethyl- or monoethylether, diethylenglykolmonomethyl- or monoethyletheror ketones such as acetone or methylisobutylketone. The solvent may also be a mixture of solvents or a mixture of a solvent or solvents with water, for example a mixture of methanol with water.

A suitable ratio by weight of such a catalyst in relation to the substrate is between 1:5 and 1:100, preferably between 1:7 and 1:15.

Heterogeneous platinum catalysts are known per se, are well described in the literature and are commercially available. It is possible to use platinum in the form of the pure metal, for example as a powder, or, what is preferred, in the form of finely distributed metal on a support. A suitable support material is for example carbon, metal oxides like $SiO_2$, $TiO_2$, $Al_2O_3$, metal salts, and natural or synthetic silicates. The catalyst may also be in the form of colloidal platinum. The amount of platinum metal is for example 1 to 10% by weight, preferably 3 to 8% by weight, relative to the support.

The hydrogenation is carried out for example with a hydrogen pressure of up to 200 bar, preferably with a hydrogen pressure of 1 to 200 bar and most preferred with a hydrogen pressure of 5 to 40 bar.

The reaction is carried out, for example, at a temperature between 0 and 80° C., especially between 20 to 25° C.

Suitable magnesium salts are the customary salts in hydrated or pure form, for example magnesium acetate, magnesium chloride, magnesium bromide, magnesium ascorbate, magnesium gluconate, magnesium stearate, magnesium nitrate, magnesium sulfate and magnesium citrate whereby magnesium acetate (especially as the tetrahydrate) is particularly preferred.

A suitable ratio by weight of the magnesium salt to the heterogeneous platinum catalyst in the instant process is from 10:1 to 1:10, preferably from 5:1 to 1:5, and most preferred from 5:1 to 1:2, whereby for above calculation purpose the magnesium salt is in the form of magnesium acetate and the heterogeneous catalyst is in the form of a carbon support with 5% by weight of platinum.

A further aspect of the instant invention is the process, wherein a compound of formula (I)

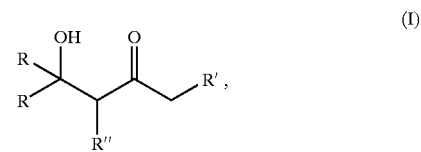

wherein R, R' and R'' are independently of each other a radical being compatible with the reaction conditions, is reduced with hydrogen to the corresponding diol, which is predominantly in the form of the syn-diol, in the presence of a magnesium salt and a heterogeneous platinum catalyst in a solvent, whereby a catalytic amount of an oxidant is added to the reaction mixture. The definitions, preferences and reaction conditions given above are also valid for this aspect of the invention.

Suitable oxidants are, for example, ozone, organic or inorganic peroxides and preferably air, oxygen or $H_2O_2$ (most preferred 30% $H_2O_2$ in water), whereby the oxidant is added to a suspension of substrate and catalyst prior to pressurizing with hydrogen. Preferably such catalytic amount is 1 to 100 µl $H_2O_2$ per 100 mg of substrate used (or the respective molar equivalent in case of a different oxidant).

Compounds of formula (I) are preferred wherein one radical R is H, R" is H and R or R' is —C(=O)$OR_b$ and $R_b$ is H or a carboxy-protecting group.

Compounds of formula (I) are preferred wherein one radical R is H, R" is H and R is —C(=O)$OR_b$; R' is substituted or unsubstituted alkyl or substituted or unsubstituted aryl and $R_b$ is H or a carboxy-protecting group.

Compounds of formula (I) are preferred wherein one radical R is H or lower alkyl and the other radical R is H, alkyl or aryl, R' is —$CO_2R_4$, —C(O)$NH_2$, —C(O)$NHR_4$ or —C(O)$NR_4R_5$, $R_4$ and $R_5$ are independently from each other alkyl and R" is H, $C_1$–$C_{12}$-alkyl), cycloalkyl or aryl.

Compounds of formula (I) are preferred wherein one radical R is H or lower alkyl and the other radical R is —$CH_2CO_2R_4$, —$CHR_4CO_2R_5$, —$CO_2R_4$, —$CH_2C(O)NH_2$, —$CH_2C(O)NHR_4$, —$CH_2C(O)NR_4R_5$, —$CHR_4C(O)NH_2$, —$CHR_4C(O)NHR_5$, —$CHR_4C(O)NR_5R_6$, —C(O)—$NH_2$, —C(O)—$NHR_4$ or —C(O)—$NR_4R_5$;

R' is substituted or unsubstituted alkyl or substituted or unsubstituted aryl;

$R_4$, $R_5$ and $R_6$ are independently from each other alkyl and

R" is H, $C_1$–$C_{12}$-alkyl, cycloalkyl or aryl.

EXAMPLES

H1

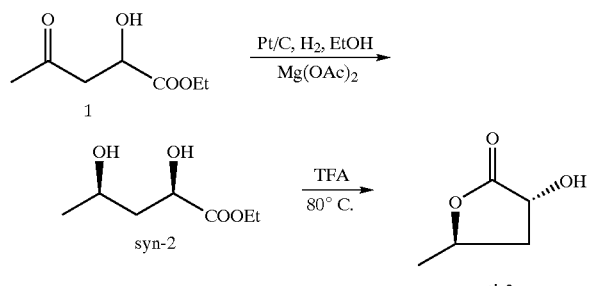

100 mg of 5% Pt/C (Engelhard 4709) and 100 mg of Mg(OAc)$_2$.4H$_2$O are placed in a 2.5 ml vial equipped with a small magnetic stirring bar. After the addition of 1 ml of EtOH, 100 µl of substrate 1 are added. The vial is placed in a 50 ml autoclave, the autoclave is sealed, purged with argon (3 times) and with hydrogen (3 times). Then the autoclave is pressurized to 20 bar with hydrogen and the magnetic stirring is started. The reaction is run for 19 h at room temperature (20 to 25° C.). Then the pressure is released, and the autoclave is purged with argon. The product is filtered and evaporated to dryness giving a mixture of 2 and 3 in quantitative yield. This mixture is dissolved in 2 ml of toluene. After the addition of 20 µl of trifluoroacetic acid, the mixture is stirred at 80° C. overnight. The reaction mixture is again evaporated to dryness and analyzed by $^{13}$C NMR.

Product identification was performed by comparison with literature data: Blandin, V.; Carpentier, J.-F.; Mortreux A.; Eur. J. Org. Chem. 1999, 1787. Results: Analysis of the $^{13}$C NMR shows 100% conversion and a 30:70 ratio of syn:anti lactone 3, resulting from a 70:30 syn:anti diol mixture.

H2

The reaction is carried out as described in H1, but without the addition of the Mg(OAc)$_2$.4H$_2$O salt. Results: The analysis of the $^{13}$C NMR shows 100% conversion and a 43:57 ratio of syn:anti lactone 3, resulting from a 57:43 syn:anti diol mixture.

H3–H6

Table 1 lists conversions of several experiments to show the accelerating effect of Mg(OAc)$_2$.4H$_2$O. The conditions are identical to the ones described for H1 and H2, except for the changes noted in Table 1.

TABLE 1

| Example | Catalyst [mg] | Additive | Additive [mg] | time [min] | conv. 1 [%] GC |
|---|---|---|---|---|---|
| H3 | 20 | — | — | 120 | 4 |
| H4 | 20 | Mg(OAc)$_2$ · 4H$_2$O | 5 | 120 | 13 |
| H5 | 100 | — | — | 1260 | 36 |
| H6 | 100 | Mg(OAc)$_2$ · 4H$_2$O | 100 | 1260 | 97 |

H7

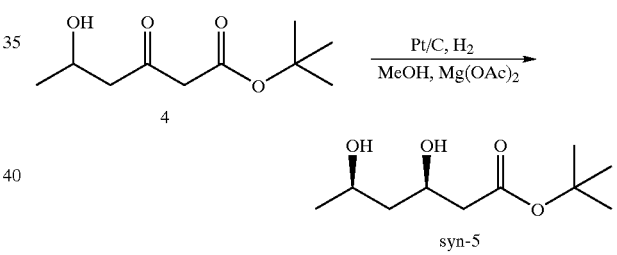

20 mg of 5% Pt/C (Engelhard 4709) and 20 mg of Mg(OAc)$_2$.4H$_2$O are placed in a 2.5 ml vial equipped with a small magnetic stirring bar. After the addition of 1 ml of MeOH, 100 µl of substrate 4 are added. The vial is placed in a 50 ml autoclave, the autoclave is sealed, purged with argon (3 times) and with hydrogen (3 times). Then the autoclave is pressurized to 20 bar and the magnetic stirring is started. The reaction is run for 3 h at room temperature (20 to 25° C.). The pressure is released, and the autoclave is purged with argon. The product is filtered and evaporated to dryness. Product identification was performed by comparison with literature data: Masoni, C.; Deschenaux, P. F.; Kallimopoulos, T.; Jacot-Guillarmod, A.; Helv. Chim. Acta 1989, 72, 1284. Conversion and diastereomeric ratio are determined by NMR and GC analysis; 5 is obtained in 83% yield with a syn:anti ratio of 6.5.

H8

The reaction is conducted as described for H7, but without the addition of the salt. Table 2 compares the results and shows the effect of the magnesium salt additive.

TABLE 2

| Example | Additive | Additive [mg] | conv. 4 [%] ($^{13}$C NMR) | Syn:anti ratio ($^{13}$C NMR) |
|---|---|---|---|---|
| H7 | Mg(OAc)$_2$ · 4H$_2$O | 20 | 83 | 6.5 |
| H8 | — | — | 18 | 1.6 |

H9–H13

Table 3 lists conversions and diastereomeric ratios of several experiments to show the influence of the catalyst type. The conditions are identical to the ones described for H7 except for the changes noted in Table 3.

TABLE 3

| Example | Catalyst type | conv. 4 [%] ($^{13}$C NMR) | Syn:anti ratio ($^{13}$C NMR) |
|---|---|---|---|
| H9 | 5% Pt/C Typ R (Degussa) | 29 | 5.0 |
| H10 | 5% Pt/C Typ F 101 (Degussa) | >95 | 7.7 |
| H11 | 5% Pt/Alox F 214_120 (Degussa) | 92 | 7.2 |
| H12 | 5% Ru/C (Engelhard 4857) | 54 | 1.1 |
| H13 | 5% Rh/C (Engelhard 4806) | 82 | 4.6 |

H14–H18

Table 4 lists conversions and diastereomeric ratios of several experiments to show the influence of the type of magnesium salt additive. The conditions are identical to the ones described for H7 except for the changes noted in Table 4.

TABLE 4

| Example | Additive | Additive [mg] | conv. 4 [%] ($^{13}$C NMR) | Syn:anti ratio ($^{13}$C NMR) |
|---|---|---|---|---|
| H14 | Mg (OOH)$_2$ | 20 | 33 | 4.8 |
| H15 | Mg(NO$_3$)$_2$ · 6H$_2$O | 24 | 33 | 6.5 |
| H16 | MgCl$_2$ · 6H$_2$O | 19 | 87 | 7.8 |
| H17 | MgBr$_2$ · 6H$_2$O | 17 | 42 | 7.7 |
| H18 | MgO | 4 | 27 | 5.0 |

H19–H22

Table 5 lists conversions and diastereomeric ratios of several experiments to show the influence of the solvent. The conditions are identical to the ones described for H7 except for the changes noted in Table 5.

TABLE 5

| Example | Solvent [1 ml] | conv. 4 [%] ($^{13}$C NMR) | Syn:anti ratio ($^{13}$C NMR) |
|---|---|---|---|
| H19 | THF | 65 | 4.5 |
| H20 | EtOH | 59 | 4.6 |
| H21 | Toluol | >95 | 3.4 |
| H22 | MeOH:H$_2$O = 9:1 | 83 | 6.5 |

H23

20 mg of 5% Pt/C (Engelhard 4709) and 20 mg of Mg(OAc)$_2$.4H$_2$O are placed in a 2.5 ml vial equipped with a small magnetic stirring bar. After the addition of 1 ml of MeOH, 100 µl of substrate 4 and 1 µl of 30% H$_2$O$_2$ solution are added. The vial is placed in a 50 ml autoclave, the autoclave is sealed, purged with argon (3 times) and with hydrogen (3 times). Then the autoclave is pressurized to 20 bar with hydrogen and the magnetic stirring is started. The reaction is run for 3 h at room temperature (20 to 25° C.). The pressure is released, and the autoclave is purged with argon. The product is filtered and evaporated to dryness. Conversion and diastereomeric ratio are determined by NMR and GC analysis; 5 is obtained in >95% yield with a syn:anti ratio of 5.4.

H24–H26

Table 6 lists conversions and diastereomeric ratios of several experiments to show the influence of the H$_2$O$_2$ additive. The conditions are identical to the ones described for H19 except for the changes noted in Table 6.

TABLE 6

| Example | Catalyst [mg] | H$_2$O$_2$ [µl] | conv. 4 [%] ($^{13}$C NMR) | Syn:anti ratio ($^{13}$C NMR) |
|---|---|---|---|---|
| H23 | 20 | 1 | >95 | 5.4 |
| H24 | 20 | 10 | >95 | 7.2 |
| H25 | 20 | 100 | >95 | 5.9 |
| H26 | 10 | 10 | 93 | 7.0 |

H27–H38

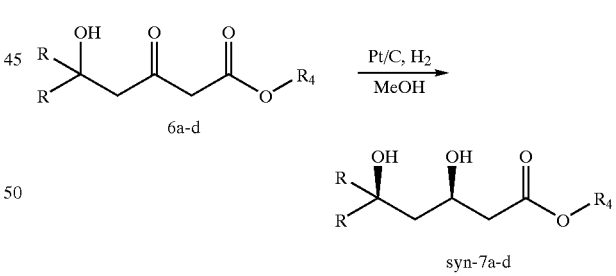

Table 7 lists conversions and diastereomeric ratios of several experiments conducted with substrates 6 differing with respect to substituents R, R' and R" to show the scope of the magnesium salt/H$_2$O$_2$ effect. The conditions are identical to the ones described for H19 except for the changes noted in Table 7. Product identification was performed by comparison with literature data: (a) Homma, K.; Takenoshita, H.; Mukaiyama, T.; *Bull. Chem. Soc. Jpn.* 1990, 63, 1898. (b) Evans, D. A.; Fitch, D. M.; Smith, T. E.; Cee, V. J.; *J. Am. Chem. Soc.* 2000, 122, 10033.

TABLE 7

| Example | Substrate | R | R | $R_4$ | Mg(OAc)$_2$ [mg] | H$_2$O$_2$ [µl] | conv. 6 [%] ($^{13}$C NMR) | Syn:anti ratio ($^{13}$C NMR) |
|---|---|---|---|---|---|---|---|---|
| H27 | 6a | phenyl | H | ethyl | — | — | 35 | 2.3 |
| H28 | 6a | phenyl | H | ethyl | 20 | — | >95 | 6.1 |
| H29 | 6a | phenyl | H | ethyl | 20 | 10 | >95 | 6.7 |
| H30 | 6b | phenyl | methyl | ethyl | — | — | 7 | 3.0 |
| H31 | 6b | phenyl | methyl | ethyl | 20 | — | 22 | 6.7 |
| H32 | 6b | phenyl | methyl | ethyl | 20 | 10 | 71 | 8.4 |
| H33 | 6c | phenyl | H | tert-butyl | — | — | 28 | 2.0 |
| H34 | 6c | phenyl | H | tert-butyl | 20 | — | 77 | 4.9 |
| H35 | 6c | phenyl | H | tert-butyl | 20 | 10 | >95 | 4.7 |
| H36 | 6d | CH$_2$OCH$_2$Ph | H | tert-butyl | — | — | 13 | 1.6 |
| H37 | 6d | CH$_2$OCH$_2$Ph | H | tert-butyl | 20 | — | 57 | 5.1 |
| H38 | 6d | CH$_2$OCH$_2$Ph | H | tert-butyl | 20 | 10 | 95 | 5.9 |

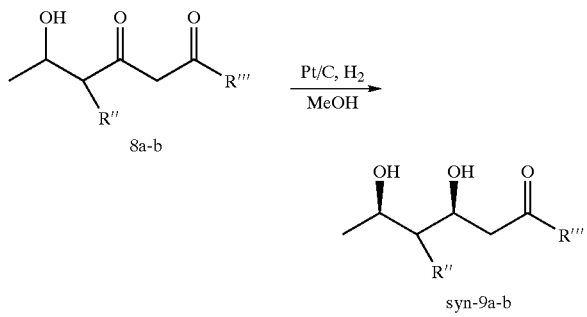

H39–H44

Table 8 lists conversions and diastereomeric ratios of several experiments conducted with substrates differing with respect to substituents R" and R'" to show the scope of the magnesium salt/H$_2$O$_2$ effect. The conditions are identical to the ones described for H19 except for the changes noted in Table 8. Product identification was performed by comparison with literature data: Evans, D. A.; Chapman, K. T.; Carreira, E. M. J. Am. Chem. Soc. 1988, 110, 3560.

respective aldehydes or ketones: Huckin, S. N.; Weiler, L.; Can. J. Chem. 1974, 22, 2157. Commercially unavailable β-ketoesters were prepared by the reaction of Meldrum's acid with the respective acid chloride: Oikawa, Y.; Sugano, K.; Yonemitsu O.; J. Org. Chem. 1978, 10, 2087. The stereochemical assignment of syn and anti descriptors for product 9b was confirmed by preferential reaction of the syn-diols (especially the minor) of the product mixture into the respective para-methoxybenzylidene acetals, whereas the anti-diols were largely left unaffected by the reaction conditions: Evans, D. A.; Ng, H. P. Tetrahedron Lett. 1993, 34, 2229.

NMR measurements were performed on a Bruker 300 MHz apparatus; GC analyses were conducted with a Carlo Erba GC 6000 equipped with a β-Dex 110 column 30 m×0.25 mm (Supelco); H$_2$ was used as the carrier gas. Injector temperature: 220° C. Detector temperature: 250° C.

Analysis Data for Compounds 3; 5, 7a–d, 9a–b
Anti-5-hydroxy-3-methyl-tetrahydrofuran-2-one, anti-3:
$^1$H-NMR (300.13 MHz; CDCl$_3$): δ 1.38 (d, CH$_3$, J=7.8 Hz); 2.12 (m, CHH), 2.36 (m, CHH); 4.52 (m, CH); 4.79 (m, CH) ppm.
$^{13}$C-NMR: (75.47 MHz; CDCl$_3$): δ 21.43 (CH$_3$); 37.07 (CH$_2$); 67.53 (CH); 75.00 (CH); 177.59 (C=O) ppm.

TABLE 8

| Example | Substrate | R" | R'" | Mg(OAc)$_2$ [mg] | H$_2$O$_2$ [µl] | conv. 8 [%] ($^{13}$C NMR) | Syn:anti ratio ($^{13}$C NMR) |
|---|---|---|---|---|---|---|---|
| H39 | 8a | methyl | —O-tert-butyl | — | — | <5 | — |
| H40 | 8a | methyl | —O-tert-butyl | 20 | — | >95 | 4.0$^a$ |
| H41 | 8a | methyl | —O-tert-butyl | 20 | 1 | >95 | 3.9$^a$ |
| H42 | 8b | H | NEt$_2$ | — | — | 35 | 1.6 |
| H43 | 8b | H | NEt$_2$ | 20 | — | >95 | 5.0 |
| H44 | 8b | H | NEt$_2$ | 20 | 10 | >95 | 4.9 |

$^a$Ratio between sum of both syn- and sum of both anti-isomers, assuming the syn-isomers to be formed in excess.

Experimental Details

Hydrogenation reactions were performed with p.a. grade solvents in a 50 ml stainless steel autoclave positioned on a magnetic stirrer. In a typical screening run, the autoclave was loaded with four 2.5 ml glass vials to conduct four different experiments at the same time, temperature and pressure.

Commercially available compounds needed as substrates or for substrate synthesis were purchased from Fluka or Aldrich Chemicals and used without further purification. Compounds 4, 6a–d and 8a–b were synthesized by aldol type condensations of β-ketoesters or -amides and the GC: Temperature program: 105° C.: 20 min, 10° C./min to 180° C.; 180° C.: 2.5 min. $t_R$=19.51, 19.86 min.
Syn-5-hydroxy-3-methyl-tetrahydrofuran-2-one, syn-3:
$^1$H-NMR (300.13 MHz; CDCl$_3$): δ 1.45 (d, CH$_3$, J=7.4 Hz); 1.87 (m, CHH), 2.74 (m, CHH); 4.43 (m, CH); 4.76 (m, CH) ppm.
$^{13}$C-NMR: (75.47 MHz; CDCl$_3$): δ 20.88 (CH$_3$); 38.78 (CH$_2$); 69.02 (CH); 73.64 (CH); 177.93 (C=O) ppm.
GC: $t_R$=15.22, 15.98 min.
Syn-3,5-dihydroxyhexanoic acid t-butyl ester, syn-5:
$^1$H-NMR (300.13 MHz; CDCl$_3$): δ 1.20 (d, CH$_3$, J=6.2 Hz); 1.46 (s, C(CH$_3$)$_3$); 1.53 (m, CH$_2$); 2.40 (d, CH$_2$, J=6.3 Hz); 3.47 (s, OH); 4.08 (m, CH); 4.22 (m, CH) ppm.

¹³C-NMR: (75.47 MHz; CDCl₃): δ 24.13 (CH₃); 28.42 (C(CH₃)₃); 43.16 (CH₂); 44.22 (CH₂); 68.49 (CH); 69.37 (CH); 81.80 (C); 172.36 (C=O) ppm.

GC: Temperature program: 150° C.: 5 min, 1° C./min to 160° C.; 160° C.: 1 min, 15° C./min to 220° C., 220° C.: 1 min. $t_R$=6.58 min.

Anti-3,5-dihydroxyhexanoic acid t-butyl ester, anti-5:

¹H-NMR (300.13 MHz; CDCl₃): δ 1.23 (d, CH₃, J=6.2 Hz); 1.46 (s, C(CH₃)₃); 1.55 (m, CH₂); 2.40 (d, CH₂, J=6.3 Hz); 3.47 (s, OH); 4.10 (m, CH); 4.24 (m, CH) ppm.

¹³C-NMR: (75.47 MHz; CDCl₃): δ 24.01 (CH₃); 28.42 (C(CH₃)₃); 42.65 (CH₂); 43.99 (CH₂); 65.22 (CH); 66.10 (CH); 81.69 (C); 172.69 (C=O) ppm.

GC: $t_R$=6.79 min.

Syn-3,5-dihydroxy-5-phenyl-pentanoic acid ethyl ester, syn-7a:

¹H-NMR (300.13 MHz; CDCl₃): δ 1.24 (t, CH₃, J=5.8 Hz); 1.75–2.00 (m, CH₂, 2 OH); 2.22 (m, CH₂); 4.16 (t, CH₂CH₃, J=5.7 Hz); 4.34 (m, CH); 4.99 (dd, CH, J=3.3, 9.6 Hz); 7.27–7.39 (m, 5 Ph—H) ppm.

¹³C-NMR: (75.47 MHz; CDCl₃): δ 14.53 (CH₃); 42.01 (CH₂); 45.15 (CH₂); 61.21 (CH₃CH₂); 68.99 (CH); 74.74 (CH); 126.12 (Ph—CH); 127.97 (Ph—CH); 128.85 (Ph—CH); 144.52 (Ph—C); 172.87 (C=O) ppm.

Anti-3,5-dihydroxy-5-phenyl-pentanoic acid ethyl ester, anti-7a:

¹H-NMR (300.13 MHz; CDCl₃): δ 1.22 (t, CH₃, J=5.8 Hz); 1.75–2.00 (m, CH₂, 2 OH); 2.24 (m, CH₂); 4.14 (q, CH₂CH₃, J=5.7 Hz); 4.34 (m, CH); 5.03 (dd, CH, J=3.2, 9.5 Hz); 7.28–7.38 (m, 5 Ph—H) ppm.

¹³C-NMR: (75.47 MHz; CDCl₃): δ 14.53 (CH₃); 41.59 (CH₂); 44.54 (CH₂); 61.21 (CH₃CH₂); 65.89 (CH); 71.48 (CH); 125.93 (Ph—CH); 127.69 (Ph—CH); 128.87 (Ph—CH); 144.78 (Ph—C); 173.18 (C=O) ppm.

Syn-3,5-dihydroxy-5-phenyl-hexanoic acid ethyl ester, syn-7b:

¹H-NMR (300.13 MHz; CDCl₃): δ 1.27 (t, CH₂CH₃, J=7.2 Hz); 1.68 (s, CH₃); 1.91 (m, CH₂); 2.45 (m, CH₂); 3.85 (d, br, 2 OH; J=7.8 Hz); 4.17 (q, CH₂CH₃, J=7.2 Hz); 4.52 (m, CH); 7.23–7.48 (m, 5 Ph—H) ppm.

¹³C-NMR: (75.47 MHz; CDCl₃): δ 14.47 (CH₃CH₂); 28.51 (CH₃); 42.15 (CH₂); 48.89 (CH₂); 61.18 (CH₃CH₂); 66.63 (CH); 74.80 (C); 124.80 (Ph—CH); 127.22 (Ph—CH); 128.60 (Ph—CH); 149.23 (Ph—C); 172.89 (C=O) ppm.

Anti-3,5-dihydroxy-5-phenyl-hexanoic acid ethyl ester, anti-7b:

¹H-NMR (300.13 MHz; CDCl₃): δ 1.18 (t, CH₂CH₃, J=5.7 Hz); 1.50 (s, CH₃); 1.98 (m, CH₂); 2.40 (m, CH₂); 3.85 (d, br, 2 OH; J=7.8 Hz); 4.14 (q, CH₂CH₃, J=7.2 Hz); 4.52 (m, CH); 7.23–7.48 (m, 5 Ph—H) ppm.

¹³C-NMR: (75.47 MHz; CDCl₃): δ 14.47 (CH₃CH₂); 30.89 (CH₃); 41.90 (CH₂); 47.80 (CH₂); 61.18 (CH₃CH₂); 66.88 (CH); 73.72 (C); 124.68 (Ph—CH); 127.04 (Ph—CH); 128.73 (Ph—CH); 147.61 (Ph—C); 172.82 (C=O) ppm.

Syn-3,5-dihydroxy-5-phenyl-pentanoic acid tert-butyl ester, syn-7c:

¹H-NMR (300.13 MHz; CDCl₃): δ 1.46 (s, C(CH₃)₃); 1.70–1.76 (m, CH₂); 2.41 (m, CH₂); 3.62 (s, br, OH); 3.84 (s, br, OH); 4.30 (m CH); 4.97 (dd, CH, J=3.0, 9.6 Hz); 7.28–7.39 (m, 5 Ph—H) ppm.

¹³C-NMR: (75.47 MHz; CDCl₃): δ 28.30 (C(CH₃)₃); 43.09 (CH₂); 45.13 (CH₂); 69.01 (CH); 74.58 (CH); 81.83 (C); 126.00 (Ph—CH); 127.87 (Ph—CH); 128.79 (Ph—CH); 144.59 (Ph—C); 172.28 (C=O) ppm.

Anti-3,5-dihydroxy-5-phenyl-pentanoic acid tert-butyl ester, anti-7c:

¹H-NMR (300.13 MHz; CDCl₃): δ 1.45 (s, C(CH₃)₃); 1.76–2.00 (m, CH₂); 2.43 (m, CH₂); 3.62 (s, br, OH); 3.84 (s, br, OH); 4.26 (m CH); 5.04 (m, CH); 7.27–7.35 (m, 5 Ph—H) ppm.

¹³C-NMR: (75.47 MHz; CDCl₃): δ 28.30 (C(CH₃)₃); 42.69 (CH₂); 44.62 (CH₂); 65.98 (CH); 71.31 (CH); 81.83 (C); 125.92 (Ph—CH); 127.57 (Ph—CH); 128.75 (Ph—CH); 144.92 (Ph—C); 172.61 (C=O) ppm.

Syn-3,5-dihydroxy-6-benzyloxy-hexanoic acid tert-butyl ester, syn-7d:

¹H-NMR (300.13 MHz; CDCl₃): δ 1.46 (s, C(CH₃)₃); 1.63 (m, CH₂); 2.41 (m, CH₂); 3.31 (s, br, OH); 3.45 (m, CH₂); 3.80 (s, br, OH); 4.08 (m, CH); 4.21 (m, CH); 4.56 (s, Ph—CH₂); 7.29–7.35 (m, 5 Ph—H) ppm.

¹³C-NMR: (75.47 MHz; CDCl₃): δ 28.09 (C(CH₃)₃); 38.89 (CH₂); 42.61 (CH₂); 68.25 (CH); 70.41 (CH); 73.39 (CH₂); 74.16 (CH₂); 81.33 (C); 127.77 (Ph—CH); 127.96 (Ph—CH); 128.45 (Ph—CH); 137.93 (Ph—C); 171.94 (C=O) ppm.

Anti-3,5-dihydroxy-6-benzyloxy-hexanoic acid tert-butyl ester, anti-7d:

¹H-NMR (300.13 MHz; CDCl₃): δ 1.46 (s, C(CH₃)₃); 1.65 (m, CH₂); 2.35 (m, CH₂); 3.27 (s, br, OH); 3.45 (m, CH₂); 3.80 (s, br, OH); 4.06 (m, CH); 4.23 (m, CH); 4.56 (s, Ph—CH₂); 7.27–7.34 (m, 5 Ph—H) ppm.

¹³C-NMR: (75.47 MHz; CDCl₃): δ 28.09 (C(CH₃)₃); 38.79 (CH₂); 42.50 (CH₂); 65.44 (CH); 67.56 (CH); 73.32 (CH₂); 74.38 (CH₂); 81.33 (C); 127.96 (Ph—CH); 128.02 (Ph—CH); 128.27 (Ph—CH); 137.93 (Ph—C); 172.24 (C=O) ppm.

Major syn-3,5-dihydroxy-4-methyl-hexanoic acid tert-butyl ester, major syn-9a: ¹H-NMR (300.13 MHz; CDCl₃): δ 0.95 (d, CH₃, J=7.2 Hz); 1.18 (d, CH₃, J=6.3 Hz); 1.40 (m, CH₂); 1.47 (s, C(CH₃)₃); 2.01 (s, br, 2 OH); 2.33 (m, CHH); 2.47 (m, CHH); 4.14 (m, CH); 4.24 (m, CH) ppm.

¹³C-NMR: (75.47 MHz; CDCl₃): δ 5.24 (CH₃); 21.45 (CH₃); 28.44 (C(CH₃)₃); 40.82 (CH₂); 42.59 (CH); 72.11 (CH); 73.04 (CH); 81.70 (C(CH₃)₃); 172.93 (C=O) ppm.

Minor syn-3,5-dihydroxy-4-methyl-hexanoic acid tert-butyl ester, minor syn-9a:

¹H-NMR (300.13 MHz; CDCl₃): δ 0.79 (d, CH₃, J=6.9 Hz); 1.20 (d, CH₃, J=6.6 Hz); 1.46 (s, C(CH₃)₃); 1.55 (m, CH₂); 2.01 (s, br, 2 OH); 2.36 (m, CHH); 2.51 (m, CHH); 3.82 (m, CH); 3.95 (m, CH) ppm.

¹³C-NMR: (75.47 MHz; CDCl₃): δ 13.01 (CH₃); 21.45 (CH₃); 28.32 (C(CH₃)₃); 40.62 (CH₂); 45.29 (CH); 72.03 (CH); 77.86 (CH); 81.90 (C(CH₃)₃); 173.12 (C=O) ppm.

Syn-3,5-dihydroxyhexanoic acid diethyl amide, syn-9b:

¹H-NMR (300.13 MHz; CDCl₃): δ 1.20 (m, 3 CH₃); 1.63 (m, CH₂); 2.44 (m, CH₂); 3.25 (m, CH₂CH₃); 3.35 (m, CH₂CH₃); 3.44 (s, br, 2 OH); 4.06 (m, CH); 4.26 (m, CH) ppm.

¹³C-NMR: (75.47 MHz; CDCl₃): δ 13.22 (CH₂CH₃); 14.32 (CH₂CH₃); 23.79 (CH₃); 39.70 (CH₂); 40.63 (CH₂); 42.40 (CH₂); 44.37 (CH₂); 68.13 (CH); 69.31 (CH); 171.86 (C=O) ppm.

GC: Temperature program: 120° C.: 5 min, 1° C./min to 160° C.; 160° C.: 10 min. $t_R$=39.03 min.

Anti-3,5-dihydroxyhexanoic acid diethyl amide, anti-9b:

¹H-NMR (300.13 MHz; CDCl₃): δ 1.23 (m, 3 CH₃); 1.65 (m, CH₂); 2.40 (m, CH₂); 3.25 (m, CH₂CH₃); 3.35 (m, CH₂CH₃); 3.44 (s, br, 2 OH); 4.12 (m, CH); 4.32 (m, CH) ppm.

¹³C-NMR: (75.47 MHz; CDCl₃): δ 13.22 (CH₂CH₃); 14.32 (CH₂CH₃); 24.00 (CH₃); 39.03 (CH₂); 40.74 (CH₂); 42.51 (CH₂); 45.16 (CH₂); 64.77 (CH); 66.08 (CH); 172.37 (C=O) ppm.

GC: $t_R$=39.30 min.

What is claimed is:

1. A process, wherein a compound of formula (I)

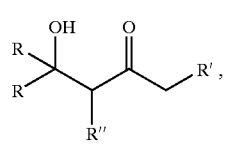

wherein R, R' and R" are independently of each other a radical being compatible with the reaction conditions, except compounds wherein a) one R is H and the other R is —CH$_2$CN, R" is H and R' is —C(=O)OR$_b$ and R$_b$ is a H or a carboxy-protecting group;

b) one R is H and the other R is —CH$_2$C(=O)NR*R**, R" is H and R' is —C(=O)OR$_b$ and R* and R** are independently of each other H or an amide-protecting group and R$_b$ is H or a carboxy-protecting group;

c) one R is H and the other R is —CH$_2$C(=O)OR$_b$, R" is H and R' is —CH$_2$—N$_3$ and R$_b$ is H or a carboxy-protecting group; and d) one R is H and the other R is —CH$_2$C(=O)OR$_b$, R" is H and R' is —CH$_2$—R$_d$ and R$_b$ is H or a carboxy-protecting group and R$_d$ is halogen;

is reduced with hydrogen to the corresponding diol, which is predominantly in the form of the syn-diol, in the presence of a magnesium salt and a heterogeneous platinum catalyst in a solvent.

2. A process according to claim 1, wherein the magnesium salt is magnesium acetate tetrahydrate.

3. A process according to claim 1 wherein the support material for the heterogeneous platinum catalyst is selected from carbon or Al$_2$O$_3$.

4. A process according to claim 1 wherein the solvent is an alcohol or a mixture of an alcohol with water.

5. A process according to claim 1 wherein for the compound of formula (I) at least one radical R is H or lower alkyl.

6. A process according to claim 1 wherein for the compound of formula (I) one radical R is H or lower alkyl and the other radical R is H, alkyl or aryl, R' is —CO$_2$R$_4$, —C(O)NH$_2$, —C(O)NHR$_4$ or —C(O)NR$_4$R$_5$, R$_4$ and R$_5$ is independently from each other alkyl and R" is H, C$_1$–C$_{12}$-alkyl), cycloalkyl or aryl.

7. A process according to claim 1 wherein for the compound of formula (I) one radical R is H or lower alkyl and the other radical R is —CH$_2$CO$_2$R$_4$, —CHR$_4$CO$_2$R$_5$, —CO$_2$R$_4$, —CH$_2$C(O)NH$_2$, —CH$_2$C(O)NHR$_4$, —CH$_2$C(O)NR$_4$R$_5$, —CHR$_4$C(O)NH$_2$, —CHR$_4$C(O)NHR$_5$, —CHR$_4$C(O)NR$_5$R$_6$, —C(O)—NH$_2$, —C(O)—NHR$_4$ or —C(O)—NR$_4$R$_5$;

R' is H, substituted or unsubstituted alkyl or substituted or unsubstituted aryl;

R$_4$, R$_5$ and R$_6$ are independently from each other alkyl and

R" is H, C$_1$–C$_{12}$-alkyl, cycloalkyl or aryl.

8. A process, wherein a compound of formula (I)

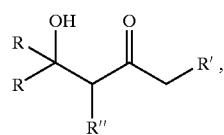

wherein R, R' and R" are independently of each other a radical being compatible with the reaction conditions, is reduced with hydrogen to the corresponding diol, which is predominantly in the form of the syn-diol, in the presence of a magnesium salt and a heterogeneous platinum catalyst in a solvent, whereby a catalytic amount of an oxidant is added to the reaction mixture.

9. A process according to claim 8 wherein the oxidant is H$_2$O$_2$ in water.

10. A process according to claim 8 wherein for the compound of formula (I) one radical R is H or lower alkyl and the other radical R is H, alkyl or aryl, R' is —CO$_2$R$_4$, —C(O)NH$_2$, —C(O)NHR$_4$ or —C(O)NR$_4$R$_5$, R$_4$ and R$_5$ is independently from each other alkyl and R" is H, C$_1$–C$_{12}$-alkyl), cycloalkyl or aryl.

* * * * *